(12) United States Patent
Patel et al.

(10) Patent No.: US 9,375,463 B2
(45) Date of Patent: Jun. 28, 2016

(54) COMPOSITIONS AND METHODS FOR IMPROVING SLEEP USING A NUTRACEUTICAL FORMULATION

(71) Applicant: Creative Medical Health Inc., Phoenix, AZ (US)

(72) Inventors: Amit Patel, Salt Lake City, UT (US); Timothy Warbington, Phoenix, AZ (US)

(73) Assignee: Creative Medical Health, Inc., Phoenix, AZ (US)

( * ) Notice: Subject to any disclaimer, the term of this patent is extended or adjusted under 35 U.S.C. 154(b) by 170 days.

(21) Appl. No.: 14/480,608

(22) Filed: Sep. 8, 2014

(65) Prior Publication Data

US 2015/0071993 A1  Mar. 12, 2015

Related U.S. Application Data

(60) Provisional application No. 61/876,158, filed on Sep. 10, 2013.

(51) Int. Cl.

| | | |
|---|---|---|
| *A61K 36/324* | (2006.01) | |
| *A61K 36/84* | (2006.01) | |
| *A61K 36/53* | (2006.01) | |
| *A61K 38/48* | (2006.01) | |
| *A61K 36/81* | (2006.01) | |
| *A61K 33/06* | (2006.01) | |
| *A61K 33/30* | (2006.01) | |
| *A61K 31/4045* | (2006.01) | |
| *A61K 31/714* | (2006.01) | |
| *A61K 36/185* | (2006.01) | |

(52) U.S. Cl.
CPC ......... *A61K 38/4873* (2013.01); *A61K 31/4045* (2013.01); *A61K 31/714* (2013.01); *A61K 33/06* (2013.01); *A61K 33/30* (2013.01); *A61K 36/185* (2013.01); *A61K 36/324* (2013.01); *A61K 36/53* (2013.01); *A61K 36/81* (2013.01); *A61K 36/84* (2013.01)

(58) Field of Classification Search
CPC ... A61K 36/81; A61K 38/4873; A61K 36/53; A61K 36/84; A61K 2300/00; A61K 31/714; A61K 36/00
See application file for complete search history.

(56) References Cited

U.S. PATENT DOCUMENTS

| | | | | |
|---|---|---|---|---|
| 6,277,396 B1 * | 8/2001 | Dente | .................... | A23L 1/3002 424/434 |
| 6,391,346 B1 * | 5/2002 | Newmark | ............. | A61K 36/185 424/733 |
| 6,955,873 B1 * | 10/2005 | Blum | .................... | A61K 31/045 435/6.16 |
| 7,521,079 B2 * | 4/2009 | Sakai | ....................... | A23K 1/14 426/433 |
| 7,691,419 B2 * | 4/2010 | DiLeva | .................. | A61K 8/678 424/725 |
| 8,377,473 B2 * | 2/2013 | Liu | ...................... | A61K 31/191 420/402 |
| 8,734,855 B2 * | 5/2014 | Liu | ...................... | A61K 31/191 420/402 |
| 2004/0161524 A1 * | 8/2004 | Sakai | ....................... | A23K 1/14 426/655 |
| 2004/0175439 A1 * | 9/2004 | Cyr | ......................... | A61K 8/97 424/725 |
| 2006/0252727 A1 * | 11/2006 | Ehrenpreis | ......... | A61K 31/7024 514/54 |
| 2007/0122492 A1 * | 5/2007 | Behr | ...................... | A61Q 17/04 424/725 |
| 2008/0016751 A1 * | 1/2008 | Frisch | ................. | A01M 23/005 43/58 |
| 2009/0004302 A1 * | 1/2009 | Cyr | ....................... | A23L 1/3002 424/732 |
| 2009/0068291 A1 * | 3/2009 | Cyr | ......................... | A61K 8/97 424/725 |
| 2009/0162304 A1 * | 6/2009 | DiLeva | .................. | A61K 8/678 424/62 |
| 2010/0173007 A1 * | 7/2010 | DiLeva | .................. | A61K 8/678 424/537 |
| 2010/0323041 A1 * | 12/2010 | Cyr | ....................... | A23L 1/3002 424/732 |
| 2011/0020443 A1 * | 1/2011 | Liu | ...................... | A61K 31/191 424/464 |
| 2011/0217753 A1 * | 9/2011 | Cyr | ......................... | A61K 8/97 435/184 |
| 2011/0311661 A1 * | 12/2011 | Behr | ...................... | A61Q 17/04 424/750 |
| 2013/0052271 A1 * | 2/2013 | Sternasty | ........... | A61K 31/7034 424/523 |
| 2013/0236542 A1 * | 9/2013 | Liu | ...................... | A61K 31/191 424/464 |

OTHER PUBLICATIONS

Balch 'Nutritional Healing'; Avery Publishing, New York, 2006, p. 723.*
Turner, L. 2007 Redo You; Better Nutrition 69.1 (Jan. 2007): 40-48, 50, 52 (8 page print out from ProQuest Database).*

* cited by examiner

*Primary Examiner* — Patricia A Leith
(74) *Attorney, Agent, or Firm* — Baumgartner Patent Law; Marc Baumgartner

(57) ABSTRACT

Provided are supplemental compositions for a nutraceutical formulation and methods for administering the same to a user for inducing or maintaining sleep as well as for alleviating pain to improve sleep using a formulation of ingredients comprising of extract of ashwagandha, extract of lavender, extract of valerian, extract of hops, melatonin, magnesium, vitamin B12, and zinc, and/or devil's claw, bromelain and boswellia.

6 Claims, No Drawings

COMPOSITIONS AND METHODS FOR IMPROVING SLEEP USING A NUTRACEUTICAL FORMULATION

CROSS REFERENCE TO RELATED APPLICATIONS

This application claims priority to Provisional Application Ser. No. 61/876,158, filed Sep. 10, 2013, and entitled "Composition and Methods for Improving Sleep Using a Nutraceutical Formulation" which is hereby expressly incorporated by reference in its entirety.

FIELD OF THE INVENTION

The present invention involves compositions and methods of using said compositions as nutritional supplements for treating insomnia and/or improving sleep quality or duration as well as for treating pain that can be a cause or consequence of insomnia.

BACKGROUND

The term "insomnia" broadly refers to an individual's report of difficulty sleeping. Insomnia has been defined in published literature as a disorder with the following diagnostic criteria: (1) Difficulty falling asleep, staying asleep or a lack of restorative sleep; (2) Persistence of sleep difficulties despite adequate opportunity and circumstances to sleep; (3) These sleep difficulties are associated with daytime impairment including cognitive, emotional or health effects; (4) Sleep impairment occurs at least 3 times per week for one month [1]. Studies estimate that 10% to 40% of American adults have intermittent insomnia and 10-15% have long-term sleep difficulties [2]. However, only approximately 5% of people with insomnia seek medical help. Cost estimates for lost productivity and insomnia-related accidents exceed $100 billion per year.

Due to its chronic nature, insomnia is associated with substantial impairments in the individual's quality of life. Individuals with insomnia score poorly on the 26-item Short Form Health Survey of the Medical Outcomes Study (SF-36) that broadly measures quality of life. One study compared the scores of patients with insomnia to those with depression and congestive heart failure and the results revealed that insomnia patients experienced a greater loss of function and increased emotional and mental health effects [3]. Several studies demonstrate a correlation between sleep deprivation and many conditions including weight gain, diabetes, depression and even an increased risk for mortality. In one published study, insomnia was associated with cognitive-emotional and cortical arousal and activation of the body's stress systems [4]. Insomnia has also been associated with decreases in work performance and increases in motor vehicle accidents and hospitalization rates [5].

According to the American Academy of Sleep Medicine (AASM) [6], a normal sleep pattern is characterized by 3 stages of non-rapid eye movement (NREM) sleep that each last between 5 and 15 minutes before REM sleep is attained, then the cycles repeat themselves. In stage 1 of NREM sleep, polysomnography readings show a reduction in wakefulness. This stage is characterized by light sleep that is easily interrupted and may also include a feeling of falling (called hypnic myoclonia). In stage 2, polysomnography shows positive and negative waves that are indicative of periods of muscle tone mixed with periods of muscle relaxation. Stage 3 is marked by deeper sleep known as slow-wave or delta sleep. Dreams can occur in Stage 3 NREM sleep, although the dreams tend to be less frequent and less memorable than those that occur during REM sleep. The next stage, REM (rapid eye movement) sleep is unlike the other sleep stages because the brain is very active. Insomnia may occur at any stage of sleep, having distinct effects depending on the nature of the disturbance. REM sleep is essential for emotional health and can be suppressed by medications such as anti-depressants. Stage 3 or slow-wave sleep is essential for physical rejuvenation and health of the immune system.

Causes of insomnia are highly variable and include the following: 1) Sleep disorders including sleep apnea and restless leg syndrome; 2) Illnesses such as asthma, congestive heart failure, hot flashes, arthritis and other causes of pain, gastrointestinal reflux disease; 3) Psychological medical conditions including depression and stress; 4) Neurological disorders including Parkinson's disease and dementia; 5) Stimulants such as caffeine and nicotine; 6) Medications including decongestants, certain anti-depressants, diuretics and beta blockers. Additionally, short-term difficulties with sleep that are not necessarily defined as "insomnia" can include inadequate opportunities for sleep; for example, caused by caring for a newborn or occupations that require long periods of alertness. Circadian rhythm sleep disorders are one of the major causes of insomnia. The suprachiasmatic nucleus in the brain is an intrinsic body clock that regulates bodily rhythms such as the sleep/wake cycle (circadian rhythm) (reviewed in [7]). The circadian clock is usually synchronized with the solar day such that cognitive function and energy levels are high in the daytime and sleep occurs at night. However, when an individual's sleep/wake pattern becomes misaligned with the body's circadian rhythm and the solar day, sleep disorders can occur. Among these are chronic insomnias, including delayed or advanced sleep phase syndrome, irregular sleep-wake cycles, and non-24-hour sleep-wake syndrome and insomnias that are temporary in nature; for example, due to jet lag or shift work. The circadian rhythm is regulated by secretion of N-acetyl-5-hydroxytryptamine (melatonin) from the pineal gland, which is induced at night and acts in the suprachiasmatic nucleus to facilitate sleep. There is evidence that circadian rhythms can be reset by phototherapy involving timed exposure to bright light [8]. Additionally, melatonin and melatonin receptor agonists have shown beneficial effects against insomnia; however, these treatments are not effective against mood disorders such as acute depression and major depressive disorder that are also associated with misaligned circadian rhythms [9].

Evaluation of insomnia includes a careful sleep history, review of medical history, review of medication use, family history, and screening for depression, anxiety and other possible variables affecting sleep. A physical examination is necessary to assess the presenting symptoms, if any. These symptoms might include snoring (possible sleep apnea), peripheral edema (heat failure), mental status (anxiety, substance abuse) or asthma. Diagnostic tests can be performed to evaluate thyroid function, abnormal hormone levels, elevated serum glucose, uremia, and iron deficiency (which could be indicative of restless legs syndrome or periodic limb movement disorder). An important diagnostic tool for insomnia is polysomnography, a diagnostic test in which physiologic sensors are place on the patients during sleep to record brain electrical activity, eye and jaws muscle movement, leg muscle movement, airflow, respiration, EKG, and oxygen saturation. One or more of these diagnostic criteria could be useful for directing an affected individual toward use of the nutraceutical composition disclosed in the present invention.

In cases where insomnia is short-term or unrelated to medical circumstances, lifestyle modifications can be implemented to aid sleep. Healthy sleep habits include maintaining a regular sleep-wake schedule and avoidance of stimulants, alcohol, and caffeine 4-6 hours before bedtime. Environmental factors such as eliminating noise, maintaining a comfortable room temperature and minimizing light are also important for promoting sleep. Stress management and relaxation therapy can also be helpful for some patients. Pharmacological approaches for inducing sleep have been centered around the activation of GABA, one of the major inhibitory neurotransmitters in the central nervous system. Drugs that have been designed to activate GABA receptors include hypnotic drugs: barbiturates, benzodiazepines, imidazopyridines, and cyclopyrrolones. Benzodiazepines are considered first-line treatments for anxiety disorders and for insomnia (temazepam [Restoril], flurazepam [Dalmane], triazolam [Halcion], estazolam [ProSom], and lorazepam [Ativan]). Benzodiazepines selectively target GABA(A) receptors that contain the alpha1, alpha2, alpha3, or alpha5 subunits, which promote sleep when stimulated [10]. Insufficient release of GABA in the brain can also lead to depression, anxiety and other mood disorders having similar symptoms of chronic insomnia. GABA is normally released during the early stages of the sleep cycle, which facilitates relaxation and restful sleep in the subsequent stages of sleep. Despite their widespread clinical use, use of benzodiazepines carries the risk of drug dependence. Moreover, these medications can have several undesirable side effects including amnesia, irritability, impaired judgment, tolerance and physical dependence. Other treatment options for insomnia are nonbenzodiazepines including zaleplon [Sonata], zolpidem [Ambien], and eszopiclone [Lunesta]). These drugs decrease sleep latency and the number of awakenings by targeting the gamma aminobutyric (GABA) receptor. The side effects of nonbenzodiazepines include drowsiness, dizziness, headache, diarrhea, nausea, and dry mouth. Sedating antidepressants (trazodone [Desyrel], mirtazapine [Remeron], paroxetine [Paxil]) can be useful if the patient is also diagnosed with depression. Ramelteon (Rozerem) is another sleep-promoting drug that is a melatonin receptor agonist that acts on receptors that regulate the sleep-wake cycle. Possible side effects of melatonin receptor agonists include nausea, dizziness, fatigue, somnolence, aggressive behavior, agitation, behavioral changes, and hallucinations. In light of the potential side effects of drugs for treating insomnia, herbal remedies that offer the possibility of having fewer unwanted side effects are also an option.

Pain represents one of the primary underlying causes of sleep disturbances. There is a circular relationship between insomnia and pain, such that pain leads to sleep disorders and sleep disorders increase the perception of pain [11]. Numerous published studies show that lack of sleep has hyperalgesic effects in intensifying pain perception [12, 13]. Insomnia associated with pain is considered to be an under-reported, under-diagnosed and under-treated problem that often symptomatic of other underlying medical and psychological causes [11]. In one study, for example, the severity of depression among veterans was independently associated with poor sleep quality and more severe pain [14].

Medications for addressing pain can have undesirable effects on sleep; therefore, treatments must be carefully considered when individuals present with both conditions. For example, certain over-the-counter medications, particularly those containing caffeine (for example, Excedrin® (formulation containing acetaminophen, aspirin and caffeine, sold by Novartis), Anacin® (formulation containing aspirin and caffeine, sold by Prestige Brands Holdings, Inc.), and Motrin Complete® (ibuprofen, sold by Johnson & Johnson Consumer Inc.)), can interfere with sleep. Narcotic pain medications, used to treat moderate to severe pain, are associated with poor sleep quality. For example, a published study reported a high rate of sleep impairment and poor sleep quality in people with prescription opiod dependence [15]. This study also demonstrated that the severity of pain, as measured by self-reporting, was correlated with poor sleep quality. Alternatively, sleep-promoting and pain medications can have additive effects, which increases the risk of side effects and adverse reactions, including excessive drowsiness and poor cognitive function the following day.

Disclosed in the present invention is a composition of ingredients that possess sleep-promoting and anti-anxiety effects, as well as methods for administering said composition to promote sleep and to reduce anxiety.

SUMMARY OF THE INVENTION

This invention teaches a composition and methods for delivering said composition for treating insomnia and for relieving pain in order to improve sleep. In one embodiment, a combination of ingredients consisting of an extract of ashwagandha, an extract of lavender, an extract of valerian, an extract of hops, melatonin, magnesium, vitamin B12 and zinc is delivered orally in capsules as a nutraceutical formulation. In another embodiment, insomnia and pain are treated concomitantly using a nutraceutical formulation that also includes extracts of devil's claw, bromelain, and boswellia.

The composition of said nutraceutical formulation contains ashwaghanda (*Withania somnifera*), and herb used in Ayurvedic (traditional Indian) medicine for addressing numerous physical and mental health issues [16]. The name "*somnifera*" in Latin means "sleep-inducer", probably referring to the extensive use of ashwagandha to promote sleep. Ashwagandha has also been referred to as Indian ginseng, since it is used to treat a variety of medical conditions similar to use of ginseng in China. Ashwagandha originates from an evergreen shrub native to the Middle East and eastern Africa. The methods for preparation of extracts of Ashwaghanda are known in the art. For example, Ashwaghanda root can be washed, dried (in an oven or by air), and pulverized with a mortar and pestle. The material can then be subjected to extraction with methanol (60° C.) in a Soxhlet apparatus for 4-5 days. This preparation can then be incorporated into capsules or into a liquid for oral administration.

Ashwagandha is considered by herbalists to be an "adaptogen": a substance that has the ability to help the body adjust to stressful situations [17]. Adaptogens have effects on the human body that assist in maintaining equilibrium in response to physical, psychological, emotional or environmental stress. Accordingly, ashwagandha has been used for more than 2, 500 years to address a range of medical issues including improving physical energy and endurance, improving immune function and providing resistance against ailments. Adaptogens such as ashwagandha can be utilized as supplements as part of a daily regimen to reduce psychological and physical stress in an individual. Alternatively, adaptogens can be utilized for the treatment of specific conditions, either alone or in combination with other herbal ingredients, vitamins, minerals, and/or nutritional supplements administered in a variety of other forms. In the context of the present invention, the term "adaptogen" specifically refers an ingredient to combat stress in the body. Administration of an adaptogen such as ashwagandha is herein described as a method for reducing stress in the body in order to enhance the specific actions of a mixture of ingredients consisting of lavender, valerian, hops, magnesium, melatonin, vitamin B12, zinc and calcium for promoting sleep and reducing anxiety.

The "non-specific" ability of adaptogens such as ashwagandha to increase resistance of the body to breadth of adverse biological, chemical, and physical stressors has been attributed to several biological activities of these substances. Adaptogens are known to regulate the functions of the adrenal glands, helping to control their production of stress hormones. "Adrenal fatigue" or hypoadrenia occurs when the adrenal glands become exhausted due to intense or prolonged stress, and are unable to keep up with the production of essential hormones for regulating energy storage, production, immune function, muscle tone and heart rate. Adaptogens promote efficient adrenal gland function by improving energy utilization by cells and preventing oxidative damage. Many adaptogens including ashwagandha [18] have anti-oxidant activity. Anti-oxidants scavenge free radicals, thereby eliminating reactive oxygen and nitrogen species that contribute to numerous chronic diseases by compromising DNA repair and cellular longevity.

Clinical studies support the efficacy of Ashwaghanda as a remedy to promote relaxation and to reduce stress, which can have beneficial effects on sleep. A prospective randomized double-blind placebo-controlled study has been conducted in 64 patients with a history of chronic stress [19]. The treatment group received 300 mg of extract of ashwaghanda root in capsules and exhibited a significant reduction on scores of stress compared to individuals who received placebo capsules. Stress was measured on the basis of standard stress-assessment questionnaires and serum cholesterol levels. In another study, 75 subjects were randomized into groups that received either naturopathic care (dietary counseling, deep breathing relaxation intervention, a multi-vitamin and ashwaghanda root (300 mg b.i.d.) [20]. The results showed that stress scores as measured with the Beck Anxiety Inventory, were significantly reduced in the naturopathic group (56.5%, p<0.0001), and to a greater extent that in the psychotherapy group (30.5%, p<0.0001). The authors concluded that naturopathic care including ashwaghanda affords significant improvements in the quality of life of patients with anxiety. Another clinical study also supported the anti-anxiety effects of ashwaghanda. An ethanolic extract of ashwaghanda was found to have beneficial effects in 88.2% of patients (n=20) with anxiety disorders compared to placebo [21].

The composition of said nutraceutical formulation also contains lavender (*Lavender officinalis* L.) Lavender has been scientifically shown to have a role in alleviating insomnia. In a study where lavender aromatherapy was given to 67 women for 12 weeks, significant improvements in sleep quality were reported [22]. In a small pilot study, patients with mild insomnia also experienced improved sleep resulting from lavender aromatherapy [23]. In human studies, one method of assessing sleep quality in the aforementioned studies involves the Pittsburgh Sleep Quality Index (PSQI), a self-rated questionnaire that evaluates sleep quality and disturbances over a one month period based on seven component scores: subjective sleep quality, sleep latency, sleep duration, habitual sleep efficiency, sleep disturbances, use of sleep medication and daytime dysfunction [24].

It is known in the art that lavender can be administered orally in capsules, by olfaction (aromatherapy), or as a tincture. Lavender oil is prepared by distillation from the flower spikes of lavender. Like all essential oils, lavender oil is a mixture of phytochemicals including linalool and linalyl acetate as well as many others, which can be administered in capsule form or as aromatherapy. It is known in the art that lavender can also be prepared as a tincture, which is a concentrated herbal extract of lavender that can also be utilized for promoting sleep and relieving anxiety. Tinctures are commonly used in the art owing to their Briefly, a lavender tincture is prepared using fresh, chopped or powdered herbs that are put into a glass container with alcohol (40% or 80 proof) and sealed until the steeping time is completed. The tincture is then strained, decanted into a tincture bottle and can be stored for up to five years. These various forms of lavender have each been utilized for treating insomnia and/or as relaxants or anxiolytic agents. For example, Lasea capsules containing lavender oil that are approved as an anxiolytic in Germany based on their comparable anti-anxiety effects as low-dose lorazepam [25].

The composition of said nutraceutical formulation also contains valerian (*Valeriana officinalis*), a plant native to Europe and Asia whose roots are used medicinally. The mechanism of action of valerian is believed to be through the action of its key component, valerenic acid, in modulating the GABA(A) receptor to promote sleep and to alleviate restlessness [26]. Other compounds in *Valeriana offiinalis* with sedative properties have been identified, including the flavonoid, glycosidase linarin, which enhances the effects of valerenic acid [27]. Valerian has been consumed in various forms including capsules, tablets, tea, and liquid extract forms. The psychotropic effects of valerian also reportedly have a positive impact in the treatment of obsessive compulsive disorder [28].

The composition of said nutraceutical formulation also contains hops (*Humulus lupulus*), a native British plant which has been used since the early fourteenth century to make beer and represents a traditional herbal remedy for nervous disorders. In a published study where hops extract was administered to common quail, which exhibit a similar sleep-wake rhythm as humans [29]. The results showed that administration of 2 mg of hops extract decreased nocturnal activity, thereby having value as a sedative. In a study of female nurses working rotating and/or night shifts, moderate consumption of non-alcoholic beer containing hops with dinner for 14 days was observed to diminish sleep latency and to reduce anxiety in the treatment vs. control groups [30]. An anxiolytic effect of hops has also been reported in experimental studies [31]. The pharmacological activity of hops in promoting sleep is due to its content of bitter acids [32]. One mechanism of action of hops involves stimulation of glutamic acid decarboxylase (GAD) activity, an enzyme responsible for production of GABA [33].

This invention teaches a nutraceutical formulation that includes a mixture of ingredients including valerian and hops. These two herbal extracts have been traditionally used together to treat insomnia. In a multicenter, randomized, placebo-controlled study, patients were given two nightly tablets of standardized extracts of a valerian (187-mg native extracts; 5-8:1, methanol 45% m/m) and hops (41.9-mg native extracts; 7-10:1, methanol 45% m/m) combination for 28 days (n=59) [34]. The results revealed subjective improvements in sleep quality and better quality of life in patients who received valerian-hops as compared to placebo controls. In another study, a single administration of a mixture of valerian and hops in a fluid extract to subjects suffering from insomnia was shown to improve their time spent in sleep as measured by electrohypnogram [35].

The composition of said nutraceutical formulation also contains melatonin, a hormone produced in the pineal gland that regulates the sleep-wake cycle in humans and animals, and is produced as a response to the natural cycle of day and night. Melatonin can be acquired from natural sources or synthesized. Animal grade melatonin contains extracts from the pineal gland; however, it is not used clinically due to the risk of contamination by viruses or animal proteins. The alternative is synthetic melatonin, which is pharmaceutical-grade and is used in supplements. Melatonin is available as a timed-release prescription drug, Circadin® (Neurim Pharmaceuticals). This hormone may be administered orally as capsules, tablets, or liquid, sublingually, or as transdermal patches. Melatonin levels typically increase after the onset of darkness, coinciding with the body's circadian rhythms, and peak in the middle of the night between 11 pm and 3 am. Some individuals with insomnia have low levels of melatonin. It is known in the art that melatonin supplementation can improve sleep parameters in patients with insomnia.

In one published study, supplementation with 3 mg of melatonin conferred subjective improvements in sleep experiences, including reductions in the time to fall asleep, improved quality of sleep, and fewer awakenings during the night [36]. Jan et al. (1994) conducted a study on the effects of melatonin on sleeping disorders in children most of whom were neurologically disabled. Fifteen subjects were given 2-5 mg or placebo before bedtime for 7-10 days, and melatonin was found to improve sleep and moods of the affected children without any reported side effects [37]. The frequency of sleep disorders is highest in the elderly. A randomized, double blind crossover study of 12 elderly people with melatonin deficiency used controlled release melatonin (2 mg for three weeks) to measure sleep quality [38]. This study showed improvement in sleep in the melatonin-treated vs. placebo group, reduced times to fall asleep and reduced times for waking up. Lastly, Zhdanova (1995) studied the effects of melatonin supplementation (0.3 or 1.0 mg, orally) in healthy males with normal sleep patterns [39]. The results showed that melatonin decreased sleep onset latency, with the subjects falling asleep approximately 40 minutes faster than individuals given placebo.

The composition also contains magnesium, an essential mineral required by the body for numerous physiological processes including muscle and nerve function, healthy immune system, maintaining heart rhythm and for bone strength. Many foods are sources of magnesium including dark leafy vegetables, nuts and seeds, fish, beans and lentils, whole grains and avocados. It is known in the art that low levels of magnesium are associated with insomnia. A double-blind randomized clinical trial of 46 elderly subjects showed that 500 mg of magnesium daily for 8 weeks improved subjective measures of sleep in the patients and reduced the levels of serum cortisol [40], a stress hormone that is notably elevated in people suffering from sleep loss [41]. Along these same lines, magnesium supplementation can reportedly alleviate symptoms of anxiety and depression, which can also be accompanied by insomnia. Pre-clinical evidence supports a relationship between anxiety and hyper-emotional states with dietary deficiencies in magnesium [42]. In a clinical study of 5708 individuals, an inverse relationship was documented between magnesium intake and standardized depression scores [43]. Mechanistically, it is known in the art that magnesium is an N-methyl-D-aspartate (NMDA) antagonist and a GABA agonist, two critical neurotransmitter pathways that regulate sleep.

The composition of said nutraceutical formulation also contains vitamin B12. It is known in the art that vitamin B12 deficiencies are associated with numerous conditions including dementia, psychosis and mood disorders. Many of these disorders also have disturbed sleep as an underlying symptom. Effects of vitamin B12 on improving conditions involving primary insomnia have also been tested. In a published study, researchers found that vitamin B12 treatment advanced the circadian rhythm by increasing sensitivity to light in 9 subjects treated orally with vitamin B12 for 4 weeks [44]. According to another article, low vitamin B12 status during pregnancy was reportedly directly linked to excessive infant crying, which was believed to reflect inadequate maturation of the sleep-wake cycle in the infants [45].

The composition of said nutraceutical formulation also contains zinc, a trace micronutrient that is essential for numerous metabolic reactions in the body. In one report, the levels of zinc in the serum and hair were found to correlate with sleep duration in adult women [46]. Along these lines, there is clinical evidence demonstrating a positive impact of zinc supplementation in sleep quality and duration. Kordas et al. (2009) reported that infants who were given zinc supplements daily for 12 months experienced increased night sleep duration and less night waking [47]. Similarly, in adults with primary insomnia (n=22 subjects), nightly administration of melatonin, magnesium and zinc was found to improve the quality and quantity of sleep compared to placebo treatment (n=21), as measured based on the Pittsburgh Sleep Quality Index, several other self-rated questionnaires, and a wearable armband sensor for measuring total sleep time [48].

In another embodiment of the invention, a composition of ingredients consisting of lavender, valerian, hops, ashwagandha, melatonin, magnesium, vitamin B12 is combined with additional ingredients, devil's claw, bromelain, and boswellia extract, for the purpose of addressing symptoms including but not limited to insomnia associated with pain.

The herb-based composition of the present invention can be administered orally by encapsulation in oral delivery vehicles or as a component of beverages, tonics, infusions, or food alone, or in combination with other dietary supplements or therapeutics. The herb-based composition of the present invention can be used alone or further formulated with pharmaceutically acceptable compounds, vehicles, or adjuvants with a favorable delivery profile, i.e., suitable for delivery to a subject. Such compositions typically comprise the herb-based composition of the present invention and a pharmaceutically acceptable carrier. As used herein, "pharmaceutically acceptable carrier" is intended to include any and all solvents, dispersion media, coatings, antibacterial and antifungal compounds, isotonic and absorption delaying compounds, and the like, compatible with pharmaceutical administration. Oral compositions generally include an inert diluent or an edible carrier. They can be enclosed in gelatin capsules, caplets compressed into tablets, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, gummie, lozenges, chewable lozenges, beads, powders, granules, particles, microparticles, and dispersible granules. Pharmaceutically compatible binding compounds, disintegrating compounds, glidants, lubricants, sweetening compounds, flavoring compounds, and/or adjuvant materials can be included as part of the composition. The composition of the present nutraceutical formulation may be administered in a partial, i.e., fractional dose, one or more times during a 24 hour period, a single dose during a 24 hour period of time, than a double dose during a 24 hour period of time, or more an a double dose during a 24 hour period of time. Fractional, double or other multiple doses may be taken simultaneously or at different times during the 24-hour period. The doses may be uneven doses with regard to one another or with regard to the individual components at different administration times.

EXAMPLE 1

Two individuals afflicted with insomnia were treated with a nutraceutical formulation with the intention of improving sleep quality or quantity. These individuals were female (ages 37 and 50), and had each been suffering from chronic insomnia for at least 3 months.

The nutraceutical formulation contained the following combination of ingredients in capsule form: 50 mg ashwagandha powder, 50 mg lavender powder, 50 mg valerian powder, 50 mg hops powder, 37.5 mg magnesium, 1.5 mg melatonin, 0.025 mg vitamin B-12, 12.5 mg zinc, and 12.5 mg calcium. One serving consisted of two capsules taken orally with an 8 oz. glass of water at bedtime. The nutraceutical formulation was administered daily for one month. No other sleep-promoting medications (prescription or over-the-counter) or herbal/natural supplements were used during the study period.

To assess the efficacy of the nutraceutical formulation for improving symptoms of insomnia, these individuals answered the questions comprising the Pittsburgh Sleep Quality Index (PSQI), a self-rated questionnaire that assesses sleep quality and disturbances over a 1-month time interval. The results give numbers in seven categories: subjective sleep quality, sleep latency, sleep duration, habitual sleep efficiency, sleep disturbances, use of sleeping medication, and daytime dysfunction A global PSQI score of 5 or greater is indicative of a poor sleep quality.

Patients were asked to keep a daily log of their subjective sleep habits, quality, and duration, as well as their daytime functioning including sleepiness during driving, eating meals or engaging in social interactions, and enthusiasm for completing tasks throughout the day. Efficacy following a month of nutraceutical supplementation was compared to PSQI scoring prior to treatment.

For Patient 1 (37 year old female), the global PSQI score was 6 in the month before treatment and 4 at one-month post-supplementation with the nutraceutical formulation For Patient 2 (50 year old female), results of PSQI scoring were 9 and 3 in the pre- and post-treatment period, respectively.

These results suggest that a combination of natural ingredients consisting of ashwagandha, lavender, valerian, hops, magnesium, melatonin, vitamin B-12, zinc, and calcium can improve symptoms of insomnia when administered daily before bedtime.

EXAMPLE 2

A cohort of healthy volunteers suffering from insomnia took a nutraceutical formulation containing the following combination of ingredients in capsules: 50 mg ashwagandha powder, 50 mg lavender powder, 50 mg valerian powder, 50 mg hops powder, 37.5 mg magnesium, 1.5 mg melatonin, 0.025 mg vitamin B-12, 12.5 mg zinc, and 12.5 mg calcium. Each volunteer took two capsules daily at bedtime. No other sleep-promoting medications (prescription or over-the-counter) or herbal/natural supplements were used concurrently with said nutraceutical formulation.

Table I summarizes the demographics and sleep history of the volunteers. The volunteers were interviewed to provide subjective assessments of their sleep histories before treatment (including events believed to contribute to insomnia) and after treatment with the nutraceutical formulation. As shown in Table I, only 2 of 13 volunteers discontinued treatment due to lack of efficacy of the nutraceutical formulation. Incidentally, both of these volunteers initially presented with a severe back injury and attributed their insomnia to nighttime pain. The remainder of the volunteers reported beneficial effects of the nutraceutical formulation on their sleep habits and continued taking natural rest for at least 4 months.

Thus, the data support the conclusion that a nutraceutical formulation of ashwagandha, lavender, valerian, hops, magnesium, melatonin, vitamin B-12, zinc, and calcium can be used to address insomnia.

TABLE I

Self reporting of the effects of a nutracuetical formulation on insomnia in 13 volunteers

| Volunteer | Sex | Age | Self-reported problem | Months Treated | Results |
|---|---|---|---|---|---|
| 001 | M | 65 | Sleeps only 3-4 hours, nightly restlessness | 14 | Sleeping soundly 6+ hours nightly |
| 002 | M | 53 | Restless sleep, frequent awakening | 9 | Sounder, uninterrupted sleep |
| 003 | F | 33 | Restless sleep, morning grogginess | 8 | Sounder sleep, no morning grogginess |
| 004 | F | 29 | Awakens tired due to interrupted sleep | 9 | Sounder sleep, no morning grogginess |
| 005 | F | 49 | Difficulty falling asleep, other meds cause drowsiness | 13 | Falls asleep within one hour |
| 006 | M | 63 | Medical complications interfere with sleep, adverse reaction to sleep meds | 13 | Sleeping soundly |
| 007 | M | 40 | Restless sleep attributed to stress | 13 | Sleeps soundly and feels well rested. |
| 008 | F | 31 | Mother of young children, difficulty falling/staying asleep | 8 | Falls asleep quickly, uninterrupted sleep |
| 009 | F | 35 | Mother of young children, difficulty falling/staying asleep | 6 | Falls asleep within 30-60 min, no morning drowsiness |
| 010 | M | 62 | Heart surgeon with difficulty falling asleep | 8 | Falls asleep easily |
| 011 | F | 57 | Business owner with insomnia due to stress, adverse reaction to sleep meds | 4 | Falls asleep within an hour, feels rested in the morning |
| 012 | F | 33 | Back injury, severe pain causing insomnia | Not recorded | No noticeable effect reported |
| 013 | M | 29 | Back injury, severe pain causing insomnia | Not recorded | No noticeable effect reported |

REFERENCES

1. Roth, T., *Insomnia: definition, prevalence, etiology, and consequences*. J Clin Sleep Med, 2007. 3(5 Suppl): p. S7-10.
2. Kiley, J. P., *Insomnia research and future opportunities*. Sleep, 1999. 22 Suppl 2: p. S344-5.
3. Katz, D. A. and C. A. McHorney, *The relationship between insomnia and health-related quality of life in patients with chronic illness*. J Fam Pract, 2002. 51(3): p. 229-35.
4. Vgontzas, A. N., et al., *Insomnia with objective short sleep duration: The most biologically severe phenotype of the disorder*. Sleep Med Rev, 2013.
5. Meyer, T. J., *Evaluation and management of insomnia*. Hosp Pract (1995), 1998. 33(12): p. 75-8, 83-6.
6. Schulz, H., *Rethinking sleep analysis*. J Clin Sleep Med, 2008. 4(2): p. 99-103.

7. Zisapel, N., *Circadian rhythm sleep disorders: pathophysiology and potential approaches to management.* CNS Drugs, 2001. 15(4): p. 311-28.
8. Gooley, J. J., *Treatment of circadian rhythm sleep disorders with light.* Ann Acad Med Singapore, 2008. 37(8): p. 669-76.
9. Quera Salva, M. A. and S. Hartley, *Mood disorders, circadian rhythms, melatonin and melatonin agonists.* J Cent Nery Syst Dis, 2012. 4: p. 15-26.
10. Rudolph, U. and F. Knoflach, *Beyond classical benzodiazepines: novel therapeutic potential of GABAA receptor subtypes.* Nat Rev Drug Discov, 2011. 10(9): p. 685-97.
11. Stiefel, F. and D. Stagno, *Management of insomnia in patients with chronic pain conditions.* CNS Drugs, 2004. 18(5): p. 285-96.
12. Nunes, F. R., J. M. Ferreira, and L. Bahamondes, *Pain threshold and sleep quality in women with endometriosis.* Eur J Pain, 2014.
13. Engstrom, M., et al., *Sleep quality and arousal in migraine and tension-type headache: the headache-sleep study.* Acta Neurol Scand Suppl, 2014(198): p. 47-54.
14. Chapman, J. B., et al., *Sleep quality and the role of sleep medications for veterans with chronic pain.* Pain Med, 2006. 7(2): p. 105-14.
15. Hartwell, E. E., et al., *Sleep disturbances and pain among individuals with prescription opioid dependence.* Addict Behav, 2014. 39(10): p. 1537-1542.
16. Kulkarni, S. K. and A. Dhir, *Withania somnifera: an Indian ginseng.* Prog Neuropsychopharmacol Biol Psychiatry, 2008. 32(5): p. 1093-105.
17. Ven Murthy, M. R., et al., *Scientific basis for the use of Indian ayurvedic medicinal plants in the treatment of neurodegenerative disorders: ashwagandha.* Cent Nery Syst Agents Med Chem, 2010. 10(3): p. 238-46.
18. Bhattacharya, A., S. Ghosal, and S. K. Bhattacharya, *Anti-oxidant effect of Withania somnifera glycowithanolides in chronic footshock stress-induced perturbations of oxidative free radical scavenging enzymes and lipid peroxidation in rat frontal cortex and striatum.* J Ethnopharmacol, 2001. 74(1): p. 1-6.
19. Chandrasekhar, K., J. Kapoor, and S. Anishetty, *A prospective, randomized double-blind, placebo-controlled study of safety and efficacy of a high-concentration full-spectrum extract of ashwagandha root in reducing stress and anxiety in adults.* Indian J Psychol Med, 2012. 34(3): p. 255-62.
20. Cooley, K., et al., *Naturopathic care for anxiety: a randomized controlled trial ISRCTN78958974.* PLoS One, 2009. 4(8): p. e6628.
21. Andrade, C., et al., *A double-blind, placebo-controlled evaluation of the anxiolytic efficacy ff an ethanolic extract of withania somnifera.* Indian J Psychiatry, 2000. 42(3): p. 295-301.
22. Chien, L. W., S. L. Cheng, and C. F. Liu, *The effect of lavender aromatherapy on autonomic nervous system in midlife women with insomnia.* Evid Based Complement Alternat Med, 2012. 2012: p. 740813.
23. Lewith, G. T., A. D. Godfrey, and P. Prescott, *A single-blinded, randomized pilot study evaluating the aroma of Lavandula augustifolia as a treatment for mild insomnia.* J Altern Complement Med, 2005. 11(4): p. 631-7.
24. Buysse, D. J., et al., *The Pittsburgh Sleep Quality Index: a new instrument for psychiatric practice and research.* Psychiatry Res, 1989. 28(2): p. 193-213.
25. Woelk, H. and S. Schlafke, *A multi-center, double-blind, randomised study of the Lavender oil preparation Silexan in comparison to Lorazepam for generalized anxiety disorder.* Phytomedicine, 2010. 17(2): p. 94-9.
26. Trauner, G., et al., *Modulation of GABAA receptors by valerian extracts is related to the content of valerenic acid.* Planta Med, 2008. 74(1): p. 19-24.
27. Fernandez, S., et al., *Sedative and sleep-enhancing properties of linarin, a flavonoid-isolated from Valeriana officinalis.* Pharmacol Biochem Behav, 2004. 77(2): p. 399-404.
28. Pakseresht, S., H. Boostani, and M. Sayyah, *Extract of valerian root (Valeriana officinalis L.) vs. placebo in treatment of obsessive-compulsive disorder: a randomized double-blind study.* J Complement Integr Med, 2011. 8.
29. Franco, L., et al., *The sedative effects of hops (Humulus lupulus), a component of beer, on the activity/rest rhythm.* Acta Physiol Hung, 2012. 99(2): p. 133-9.
30. Franco, L., et al., *The sedative effect of non-alcoholic beer in healthy female nurses.* PLoS One, 2012. 7(7): p. e37290.
31. Zanoli, P., et al., *New insight in the neuropharmacological activity of Humulus lupulus L.* J Ethnopharmacol, 2005. 102(1): p. 102-6.
32. Schiller, H., et al., *Sedating effects of Humulus lupulus L. extracts.* Phytomedicine, 2006. 13(8): p. 535-41.
33. Awad, R., et al., *Effects of traditionally used anxiolytic botanicals on enzymes of the gamma-aminobutyric acid (GABA) system.* Can J Physiol Pharmacol, 2007. 85(9): p. 933-42.
34. Morin, C. M., et al., *Valerian-hops combination and diphenhydramine for treating insomnia: a randomized placebo-controlled clinical trial.* Sleep, 2005. 28(11): p. 1465-71.
35. Dimpfel, W. and A. Suter, *Sleep improving effects of a single dose administration of a valerian/hops fluid extract—a double blind, randomized, placebo-controlled sleep-EEG study in a parallel design using electrohypnograms.* Eur J Med Res, 2008. 13(5): p. 200-4.
36. Spong, J., et al., *Melatonin supplementation in patients with complete tetraplegia and poor sleep.* Sleep Disord, 2013. 2013: p. 128197.
37. Jan, J. E., H. Espezel, and R. E. Appleton, *The treatment of sleep disorders with melatonin.* Dev Med Child Neurol, 1994. 36(2): p. 97-107.
38. Garfinkel, D., et al., *Improvement of sleep quality in elderly people by controlled-release melatonin.* Lancet, 1995. 346(8974): p. 541-4.
39. Zhdanova, I. V., et al., *Sleep-inducing effects of low doses of melatonin ingested in the evening.* Clin Pharmacol Ther, 1995. 57(5): p. 552-8.
40. Abbasi, B., et al., *The effect of magnesium supplementation on primary insomnia in elderly: A double-blind placebo-controlled clinical trial.* J Res Med Sci, 2012. 17(12): p. 1161-9.
41. Leproult, R., et al., *Sleep loss results in an elevation of cortisol levels the next evening.* Sleep, 1997. 20(10): p. 865-70.
42. Sartori, S. B., et al., *Magnesium deficiency induces anxiety and HPA axis dysregulation: modulation by therapeutic drug treatment.* Neuropharmacology, 2012. 62(1): p. 304-12.
43. Jacka, F. N., et al., *Association between magnesium intake and depression and anxiety in community-dwelling adults: the Hordaland Health Study.* Aust N Z J Psychiatry, 2009. 43(1): p. 45-52.
44. Honma, K., et al., *Effects of vitamin B12 on plasma melatonin rhythm in humans: increased light sensitivity phase-advances the circadian clock?* Experientia, 1992. 48(8): p. 716-20.

45. Goedhart, G., et al., *Maternal vitamin B-12 and folate status during pregnancy and excessive infant crying*. Early Hum Dev, 2011. 87(4): p. 309-14.
46. Song, C. H., Y. H. Kim, and K. I. Jung, *Associations of zinc and copper levels in serum and hair with sleep duration in adult women*. Biol Trace Elem Res, 2012. 149(1): p. 16-21.
47. Kordas, K., et al., *The effects of iron and/or zinc supplementation on maternal reports of sleep in infants from Nepal and Zanzibar*. J Dev Behav Pediatr, 2009. 30(2): p. 131-9.
48. Rondanelli, M., et al., *The effect of melatonin, magnesium, and zinc on primary insomnia in long-term care facility residents in Italy: a double-blind, placebo-controlled clinical trial*. J Am Geriatr Soc, 2011. 59(1): p. 82-90.

The invention claimed is:

1. A composition for promoting sleep and/or alleviating pain, wherein said composition consists of 50-200 mg ashwagandha, 50-200 mg lavender, 50-200 mg hops, 50-200 mg valerian, 1-3 mg melatonin, 25-100 mg magnesium, 10-50 mcg vitamin B12, 10-50 mg zinc, 10-50 mg calcium, 50-200 mg devil's claw, 50-200 mg bromelain, and 50-200 mg boswellia and wherein the composition is in the form of a tablet or capsule.

2. A method for promoting sleep and/or alleviating pain, comprising administering to a mammal in need thereof the composition of claim 1.

3. The method of claim 2, wherein said composition is administered orally.

4. The method of claim 2, wherein the method is for promoting sleep.

5. The method of claim 4, wherein administration comprises administering the composition to the mammal twice within 90 minutes before the mammal attempts to fall asleep.

6. The method of claim 4, wherein the mammal is suffering from insomnia caused by one or more of the following disorders: circadian rhythm sleep disorder, parasomnia, somniphobia, generalized anxiety disorder, obsessive compulsive disorder, panic disorder, post-traumatic stress disorder, depression, and chronic stress.

* * * * *